(12) United States Patent
Bzostek et al.

(10) Patent No.: US 11,684,451 B2
(45) Date of Patent: *Jun. 27, 2023

(54) THERMO-ELECTRIC GENERATOR

(71) Applicant: Medtronic Navigation, Inc., Louisville, CO (US)

(72) Inventors: Andrew Bzostek, Boulder, CO (US); Vince J. Doerr, Boulder, CO (US); Brad Jacobsen, Erie, CO (US); Duane Smith, Glendale, AZ (US)

(73) Assignee: Medtronic Navigation, Inc., Lafayette, CO (US)

( * ) Notice: Subject to any disclaimer, the term of this patent is extended or adjusted under 35 U.S.C. 154(b) by 398 days.

This patent is subject to a terminal disclaimer.

(21) Appl. No.: 16/936,644

(22) Filed: Jul. 23, 2020

(65) Prior Publication Data

US 2020/0352677 A1    Nov. 12, 2020

Related U.S. Application Data

(62) Division of application No. 14/674,630, filed on Mar. 31, 2015, now Pat. No. 10,722,320.

(51) Int. Cl.
*A61B 90/00* (2016.01)
*A61B 90/70* (2016.01)
(Continued)

(52) U.S. Cl.
CPC .............. *A61B 90/70* (2016.02); *A61B 17/00* (2013.01); *A61B 34/20* (2016.02); *A61L 2/04* (2013.01);
(Continued)

(58) Field of Classification Search
CPC ......... A61B 90/70; A61B 17/00; A61B 34/20; A61B 17/16; A61B 2017/00473;
(Continued)

(56) References Cited

U.S. PATENT DOCUMENTS

| | | |
|---|---|---|
| 4,292,579 A | 9/1981 | Constant |
| 6,434,507 B1 | 8/2002 | Clayton et al. |

(Continued)

FOREIGN PATENT DOCUMENTS

| | | |
|---|---|---|
| EP | 2124267 A2 | 11/2009 |
| WO | 2013/044157 A1 | 3/2013 |

OTHER PUBLICATIONS

International Search Report and Written Opinion dated Jun. 24, 2016 for PCT/US2016/023867 which claims the benefit of U.S. Appl. No. 14/674,630, filed Mar. 31, 2015.

(Continued)

*Primary Examiner* — Joel Lamprecht
(74) *Attorney, Agent, or Firm* — Harness, Dickey & Pierce, P.L.C.

(57) ABSTRACT

Disclosed herein, a power supply may be recharged with a generally used system. In various embodiments, cleaning systems may be used to affect a generator to cause the generator to charge a power supply. Such charging systems may be used without the need for separate or specialized power charging systems. A charging source or system may, therefore, also charge a power supply without requiring additional steps.

12 Claims, 3 Drawing Sheets

(51) Int. Cl.
  *A61B 34/20* (2016.01)
  *A61B 17/00* (2006.01)
  *H02J 50/10* (2016.01)
  *A61L 2/04* (2006.01)
  *H04B 5/00* (2006.01)
  *A61B 17/16* (2006.01)
  *H10N 10/10* (2023.01)

(52) U.S. Cl.
  CPC ............ *H02J 50/10* (2016.02); *H04B 5/0037* (2013.01); *A61B 17/16* (2013.01); *A61B 2017/00473* (2013.01); *A61B 2017/00734* (2013.01); *A61B 2034/2051* (2016.02); *A61B 2034/2068* (2016.02); *A61B 2034/2072* (2016.02); *A61B 2090/0813* (2016.02); *A61B 2090/363* (2016.02); *H10N 10/10* (2023.02)

(58) Field of Classification Search
  CPC .. A61B 2017/00734; A61B 2034/2051; A61B 2034/2068; A61B 2034/2072; A61B 2090/0813; A61B 2090/363; A61L 2/04; H02J 50/10; H04B 5/0037; H01L 35/28
  See application file for complete search history.

(56) References Cited

U.S. PATENT DOCUMENTS

| | | | |
|---|---|---|---|
| 6,620,994 | B2 | 9/2003 | Rossi |
| 8,644,907 | B2 | 2/2014 | Hartmann et al. |
| 9,405,085 | B2 | 8/2016 | Ramachandran et al. |
| 10,722,320 | B2 * | 7/2020 | Bzostek .................. A61B 34/20 |
| 2004/0000713 | A1 | 1/2004 | Yamashita et al. |
| 2010/0076455 | A1 | 3/2010 | Birkenbach et al. |
| 2011/0237937 | A1 | 9/2011 | Kalpin et al. |
| 2012/0046542 | A1 | 2/2012 | Csavoy et al. |
| 2013/0137957 | A1 | 5/2013 | Wood et al. |
| 2014/0276703 | A1 | 9/2014 | McKay |
| 2014/0323852 | A1 | 10/2014 | Wald et al. |

OTHER PUBLICATIONS

International Preliminary Report on Patentability dated Oct. 12, 2017 in corresponding International Application No. PCT/US2016/023867.
European Office Action regarding corresponding European Patent Application No. 16716731.1, dated Oct. 17, 2019.
Office Action dated Jun. 25, 2020 in corresponding European Application No. 16716731.1.
U.S. Appl. No. 16/674,630, U.S. Pat. No. 10,722,320, filed Mar. 31, 2015, Bzostek, et al.

* cited by examiner

THERMO-ELECTRIC GENERATOR

CROSS-REFERENCE TO RELATED APPLICATIONS

This application is a divisional of U.S. application Ser. No. 14/674,630 filed on Mar. 31, 2015. The entire disclosure of the above application is incorporated herein by reference.

FIELD

The subject disclosure relates to power storage and generation systems, including, in various embodiments to generating and storing power for instruments.

BACKGROUND

This section provides background information related to the present disclosure which is not necessarily prior art.

Instruments, including various hardware instruments, surgical instruments, and the like may require power sources to operate. For example, a surgical instrument may include a powered drill that may be electrically powered. Additionally, various instruments may include a battery powered drill such as a rotary hammer drill. Systems associated with the instrument may also require power for operation that generally may include a power source, such as a battery, that may be carried with the instrument.

SUMMARY

This section provides a general summary of the disclosure, and is not a comprehensive disclosure of its full scope or all of its features.

Powered tools may require a power source. Also, however, certain tools may include additional systems that are powered in addition to the general use of the tool. For example, wireless systems may be either battery powered (i.e. including an on-board power system) or may be passive (e.g. including a radiative or inductive power system). Inductive or radiative power systems can include those disclosed in U.S. Patent Application Pub. No. 2011/0237937, published Sep. 29, 2011, incorporated herein by reference.

Disclosed herein, a power source or supply, such as a battery, may be recharged with a charging system including a thermo-electric generator. In various embodiments, cleaning systems may be used to affect the thermo-electric generator to cause the generator to charge the power source. Such charging systems may be used without the need for separate or specialized power charging systems. Further, the charge system may charge the power source without an additional step. In other words, charging may occur within a workflow operation of the tool. Thus, charging the power source requires no additional steps to charge.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
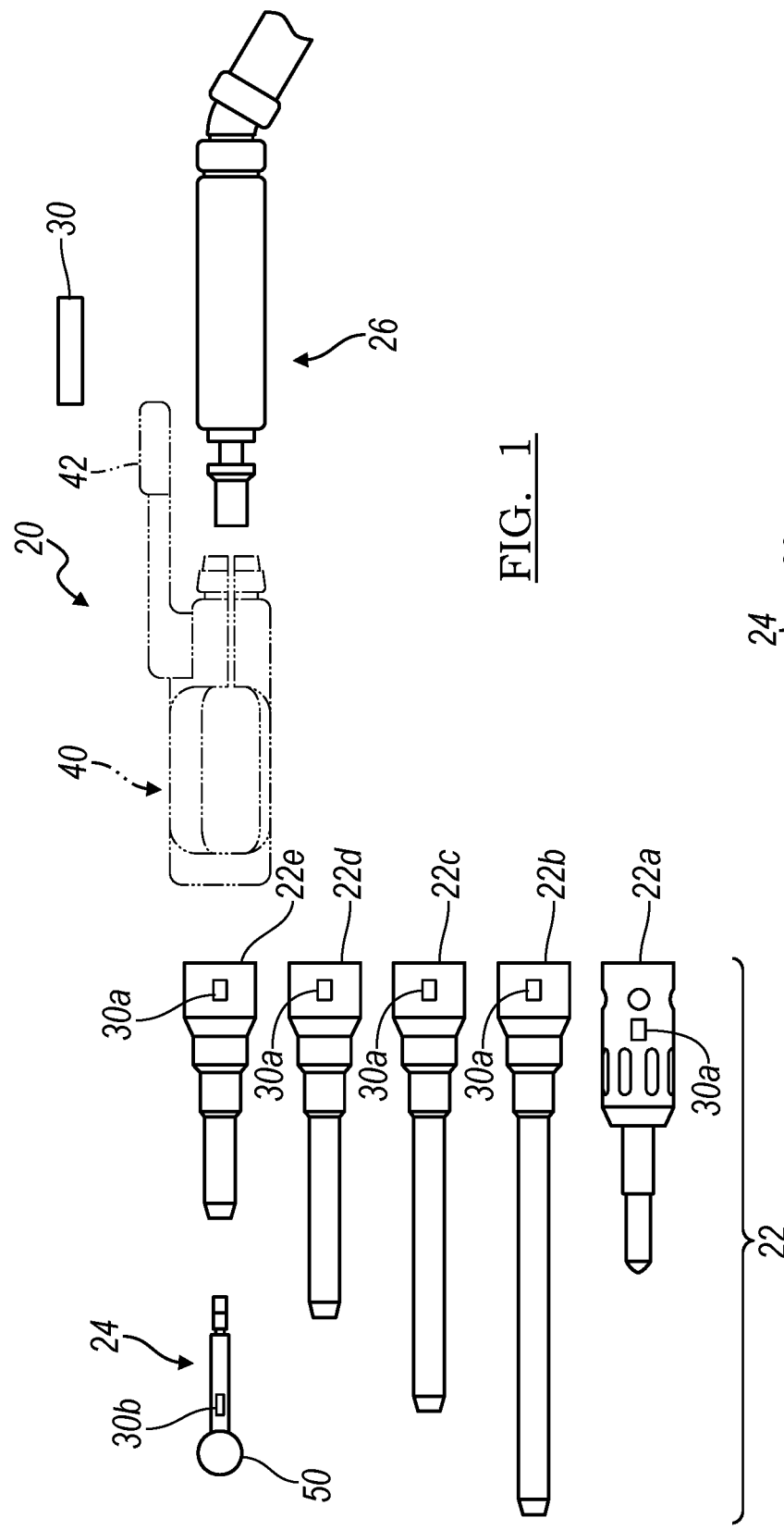
FIG. 1 is an exploded view of a tool assembly with a tracking device.

Example embodiments will now be described more fully with reference to the accompanying drawings.

Initially, it is understood that although the following disclosure relates to surgical instruments and various embodiments, that the disclosure may also relate to non-surgical instruments. Generally, a powered instrument or tool may include a power pack or power supply, such as a chemical battery, to provide an energy source to power an electrical system, such as a transmitter or sensor. Such a power source or storage system may be charged according to various techniques, such as those discussed herein, regardless of the intended use of the instrument. Therefore, it is understood that tools may be used for various procedures, such as a surgical procedure on a patient, including a human patient, a mechanical assembly or repair of a non-animate subject, or a combination thereof. In fact, it is understood that instruments that may be used for surgical procedures may also be used for non-surgical procedures.

Various instruments, such as a stylet, may include tracking devices associated that are tracked with an electromagnetic tracking system. Various other instruments can include drills, implants, suction devices, and the like may be used with various navigation systems such as the Stealth Station® 57® navigation system sold by Medtronic, Inc., having a place of business in Colorado, USA. Various tracking systems can include the AxiEm® navigation system having electromagnetic fields and trackable devices associated therewith. Generally, a trackable device may sense an electromagnetic field and transmit information regarding the sensed field to a tracking system. The transmission of information can be wired or wireless, such that the tracking device is connected with a wire or with wireless transmissions to a navigation system. Nevertheless, power may generally be provided to the tracking device to sense the field and/or transmit the sensed field to the navigation system. According to various embodiments, a battery can be connected with the tracking device to provide power to sense and/or transmit the sensed field. A generator, such as a thermal electric generator, discussed here in further detail, can be used to recharge the battery and/or replace the battery to provide power to the system transmitting the sensed field information or used to power a transmitter or an emitter, such as a coil array as used in the AxiEm® surgical navigation system sold by Medtronic, Inc.

Regardless, and according to various embodiments, a surgical instrument assembly 20 may be provided. A surgical instrument assembly 20 may be provided according to various embodiments which may include one or more attachment mechanisms 22 that are configured to couple a tool tip 24 to a tool or instrument body 26. Such systems may include those similar to that described in U.S. Pat. No. 6,434,507, incorporated herein by reference. It is understood that the several tool assembly portions, including the tool tip 24, the attachment 22, and the tool body 26 may be generally known in the art. However, as discussed further herein, various systems may be associated with these portions to allow for tracking of the tool assembly 20, including at least the tool tip 24. It is also understood that various instruments can include instruments such as those sold by Medtronic Navigation, Inc. either alone or in combination with various surgical navigation systems including the Stealth Station® surgical navigation system and the AxiEm™ navigation system. Instruments may include navigational elements including tracking elements or devices associated with the instruments. These instruments can be included in the AxiEm™ navigation stylet, AxiEm™ registration pointers, and AxiEm™ navigation probe. Further instruments can include an awl and a tap for various implants such as screws, and drills.

Nevertheless, regardless of the specific design and components of the tool assembly 20, it may include a trackable portion or device 30. The tracking device 30 may be an assembled or connected portion, as illustrated in FIG. 1 or may be integrated as a substantially non-removable portion from selected components of the tool assembly 20. Further, the tracking device may be provided as one or more tracking devices, as discussed herein. Therefore, unless specifically indicated otherwise, discussion of a tracking device herein may refer to one or more tracking devices associated with the tool assembly 20 or a portion thereof.

For example, a tracking device 30 may be integrated into one of the attachments 22 as tracking device 30*a*. Also, the tracking device 30 may be integrated into the tool tip 20 as tracking device 30*b*. It is understood that the tool assembly 20 may have one or more tracking devices, and that the illustrated tracking devices 30, 30*a*, 30*b* are merely exemplary. The tracking devices may be electromagnetic tracking devices and may be configured to be generally small in size.

For example, the tracking devices 30, 30*a*, and 30*b* can generally include a coil of wire around an axis. The coil of wire may be around a core including a ferromagnetic core, air core, or other selected core. The tracking device 30 can be configured to be associated with a respective portion of the tool assembly to assist in tracking the tool assembly. For example to integrate or include a tracking device with a standard tool, a holder 40 may optionally be provided to connect to the tool body 26 and/or the attachments 22. The holder 40 may include a connection region 42 that allows for connection of the tracking device 30 to the holder 40. Alternatively, the tracking device 30 may be connected directly to the tool body 26, and if selected, to have a removable tracking device 30. Additionally, it is understood that the attachment 22 may include a plurality of attachments 22*a*-*e* and each of the attachments 22*a*-*e* can include the tracking device 30*a* or a respective one of the tracking devices 30*a*.

As discussed further herein, the instrument assembly, including the tool tip 24, can be tracked relative to a subject, such as a human patient, and a position of the instrument assembly, for example, including the tool tip 24, can be illustrated on a display. For example, an icon or rendering of the tool assembly 20 or only the tool tip 24 can be superimposed on an image, such as a reconstructed image, of the subject. By tracking the tracking device, or a plurality of tracking devices, the position of the tool assembly may be determined. Generally, it is selected to determine a location of at least a working portion 50 of the tool tip 24. The position of the working portion 50 may include both three-dimensional coordinates (X, Y, Z), and orientation in three degrees of freedom. These components can be used to determine a location of the working portion 50 of the tool tip 24. It is also understood that the working portion of the selected instrument may include the distal end of a stylet or catheter which may not be rigidly held (i.e., the distal portion may be flexible or moveable) relative to the tool body 26 or other selected tool body.

Figure 2:
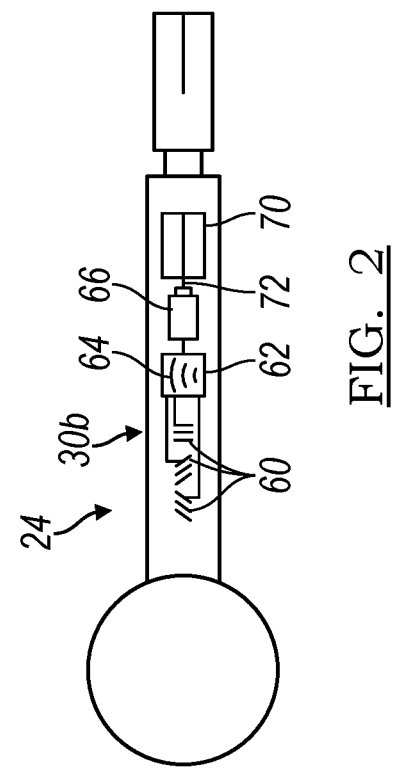
FIG. 2 is a detail view of a tool tip with the tracking device.

With continuing reference to FIG. 1 and additional reference to FIG. 2, the tool tip 24 can include the tracking device 30*b*. The tracking device 30 can include an electromagnetic (EM) tracking device including those disclosed in U.S. Pat. No. 8,644,907, incorporated herein by reference, and those included in the instruments used with the AxiEm™ surgical navigation system instruments that are tracked with the tracking system. Briefly, the tracking device 30, including the tracking device 30*b*, may include one or more coils 60 of conductive, such as electrically conductive, material, such as conductive wire. If more than one coil of wire is provided, each coil may be wound at an angle relative to the other coils to provide a greater degree of freedom information regarding the location of the tool tip 24.

Each of the coils 60 may be connected, such as with a conductor, to a transmission or transmitter portion 62, which may include a printed circuit board (PCB). The transmission portion 62 may include an antenna 64 that allows for wireless transmission of information to a tracking system and/or navigation system, as discussed further herein. Further, the transmission system 62 may include a processor to assist in transmitting the information, such as the sensed field strengths, and other appropriate processing.

Additionally, between the coils 60 and the PCB may be additional components, such as filters, amplifiers, signal processors. Also, the PCB may include additional components, such as those noted above, in addition to the antenna. As noted herein these components and the antenna 64 may require power to transmit a signal.

A power supply or power source 66, such as a battery, may provide power to the transmission portion 62, the coil 60, and/or other components included with the PCB or between the coils 60 and the transmission portion 62. The PCB may further include analog circuitry (e.g. amplifiers, filters), analog to digital converters, and digital processing circuitry (e.g. FPGA, DSP, discrete digital logic). In various examples, the digital processing circuitry may include a counter that may determine exposure to high temperatures, such as when through an autoclave cycle. The power source 66 can include a chemical battery, capacitor, LC tank circuit, or other appropriate energy storage portion. For example, capacitors or batteries may be charged with an external current for providing selected power to the transmission portion 62. The power source 66, however, may include a limited power such as enough power to provide transmission power during a selected procedure, including a single surgical procedure. Therefore, the power source 66 may be rechargeable using an exterior current provided to the power source 66.

An exterior source may provide the exterior current provided to the power source 66 and this may be exterior to the tool tip 24. The current source may be, however, only external to the power source 66, but integrated into the tool assembly 20, or separate from the tool assembly 20. In various embodiments, a thermal electric generator 70 may be incorporated into the tool tip 24. Alternatively, the generator 70 may be integrated and provided with or on another portion of the tool assembly 20. With the thermoelectric generator 70 incorporated into the tool tip 24 the battery 66 may be recharged after being drained or partially drained without requiring an external (e.g., external to the tool assembly and/or the tool tip 24) source to recharge the power source 66.

In various embodiments, the thermo-electric generator 70 may include coupled thermo-electric electrodes which may include bismuth and telluride (e.g. including tellurium). In the coupled electrodes, one electrode may be doped with palladium or selenium and the other with antimony or gold. The coupled electrodes may generate a current based upon a temperature differential between two junctions of the electrodes. The temperature differential can be generated from an external source, such as an autoclave or steam autoclave device. Various thermo-electric generators can include those disclosed in U.S. Pat. Nos. 6,620,994 and 4,292,579, both incorporated herein by reference. Various other thermo-electric generators, which may be used or augmented to provide the generator 70, can include those sold by Laird, having a place of business in Earth City, Mo. or London, England. Further, the power source 66 may include a high temperature rechargeable battery such as hose in the Thinergy Series of products, sold by Infinite Power Solutions, having a place of business at Infinite Power Solutions, Colorado. Further, it is understood that the generator 70 can be interconnected with the power source 66 via a charging connection circuitry 72. The charging connection circuitry 72 may include regulators, etc. and may be similar to that as provided by the Maxim Integrated Power and Battery Management Series, having a place of business at San Jose, Calif. or devices sold by Watronix, having a place of business in West Hills, Calif.

In various embodiments, therefore, the generator 70 may be used to create a selected current at a selected voltage to charge the battery or power source 66. The operation of the generator 70 may be separate from the operation of the tracking device 30b to determine a location of the tool tip 24. Further, it is understood, that the portions of the tracking device 30 may be separated such that the generator 70 and the power source 66 are provided a distance from portions of the tracking device 30, such as the coils. For example, the generator 70 may be on a different component of the tool assembly 20 than the tracking coils 60.

Further, the specific make-up of the generator 70 may be optimized for selected temperature differentials that may be achieved during a selected procedure, such as an autoclaving of the tool tip 24. Therefore, charging of the power source 66 with the generator 70 may proceed according to a method, as discussed further herein. For example, a voltage or current supply may be optimized to ensure that the power supply is fully or nearly fully charged during a cleaning cycle of the tool portion or assembly 20. This may consider the capacity of the power source 66, the charging circuitry 72, etc. The tracking devices 30, 30a, and 30b including the power source 66, generator 70, and other components, may also be properly packaged for operation during a procedure and recharging. As discussed herein, the recharging may occur in a high temperature and moisture environment. Thus, the tracking device 30, 30a, 30b may be liquid sealed, such as a hermetically sealed, to an external environment. Due to the recharging system, including the generator 70, the seal need not be broken to recharge the power source 66.

Figure 3:
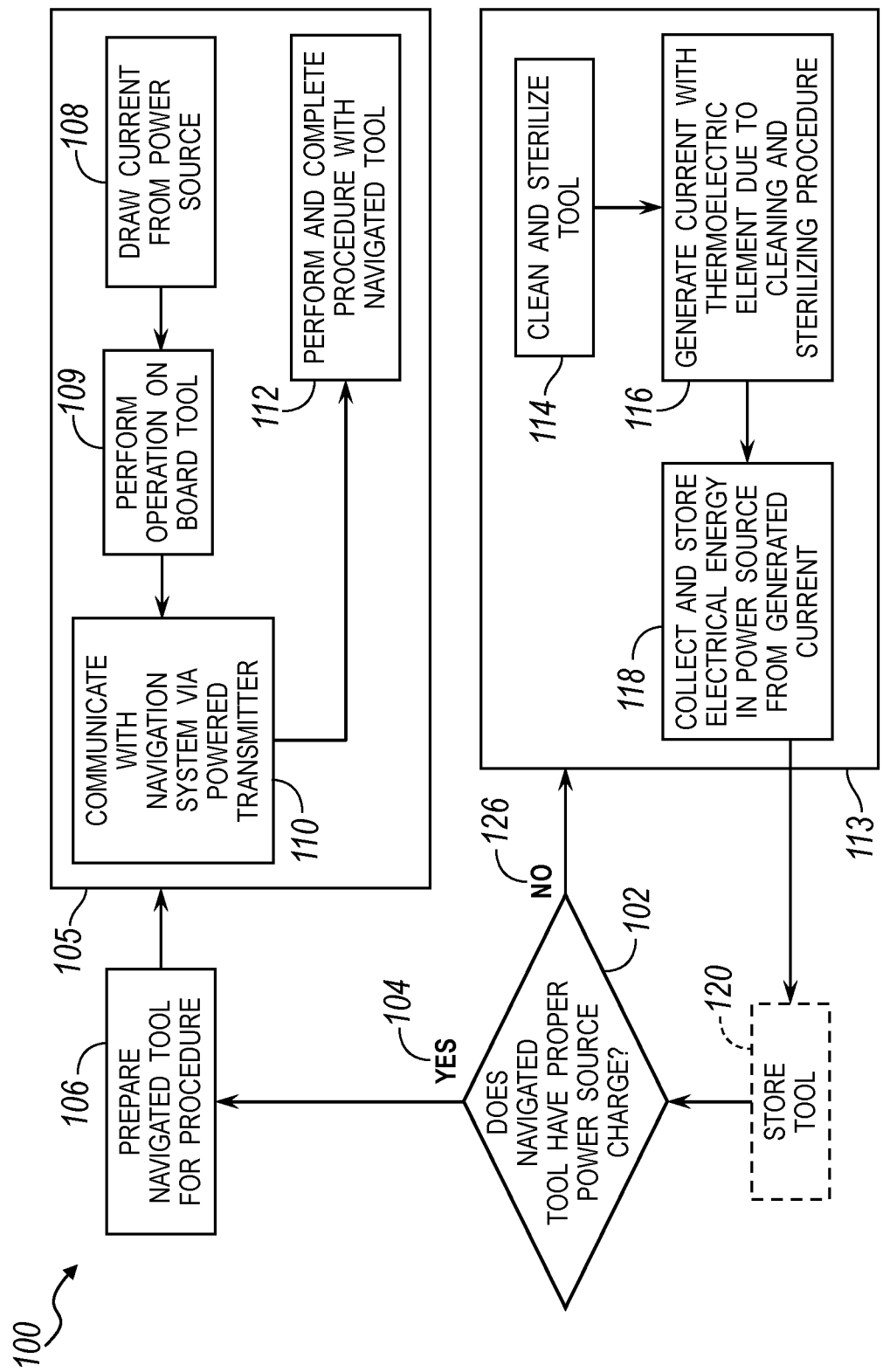
FIG. 3 is a workflow chart for charging a power supply.

Turning reference to FIG. 3, a workflow or method for using the tool assembly 20, specifically and particularly using the tracking device 30 associated with the tool assembly 20 is illustrated. It is understood that although the discussion herein refers specifically to the tracking device 30b, that the discussion may related to any appropriate tracking device. Generally, the work flow may begin at a decision block 102 to determine whether or not the power supply, such as the power source 66, has a proper charge. The determination may be made by transmission from the transmitter assembly 62 regarding a voltage of the power source 66. It is understood, however, that various other determinations may be made. Such as a duty cycle length since a last charging cycle, etc. Also, a power source charge capacity may be determined as to whether it is properly charged, such as if it is within a selected range of a selected or predetermined optimum charge amount as measured by a voltage measurement, but a specific voltage measurement may vary and be selected based upon power consumption and/or voltage requirements for various purposes. If the decision block 102 determines that the charge supply is appropriate, the "yes" path 104 may be followed to prepare a navigated tool for procedure block 106.

Preparation of the tool may include selecting the tool, assembling the tool assembly 20, or other appropriate preparation steps. For example, the particular attachment, including the attachments 22a-22e may be inputted to the navigation system, as illustrated further therein, to allow for the navigation system to determine a geometry and size of the tool assembly 20. Further, the preparation of the tool in block 106 can include ensuring the appropriate number of tools is provided for a selected procedure.

Figure 4:
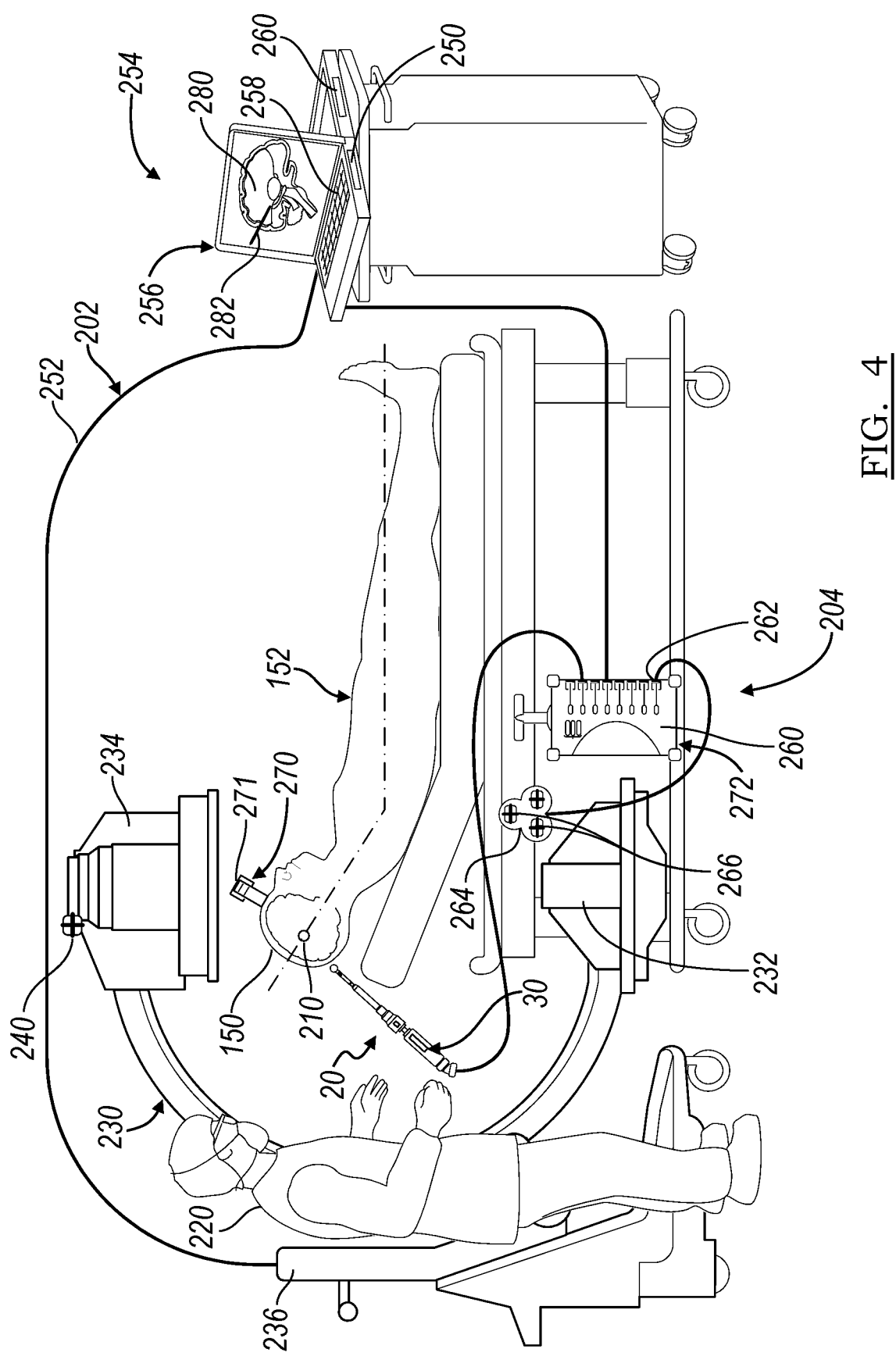
FIG. 4 is a view of a navigation and imaging system.

Following preparation of the navigated tool in block 106, a USE sub-work flow 105 may be entered. In the USE block 105 the tracking device 30b may draw current from the power source in block 108. The tracking device 30b may draw current from the power source in block 108 to communicate with the navigation system in block 109, as illustrated in FIG. 4, in block 110. Communication with the navigation system may be according to any appropriate communication mechanism, as discussed further herein, such as a wireless transmission. Further, the communication may include communicating various information that is determined or calculated by a processor on a tool. For example sense and emit energy may be communicated along with logic operations, calculations regarding uses, time in operation, etc., such as in block 109. As discussed above, the power source 66 can be connected to the transmission system 62 which may include an antenna 64 to allow for transmitting a sensed field for tracking the tool tip 24. Therefore, current may be drawn from the power source 66 to allow for communication with the navigation system in block 108.

Communication with the navigation system in block 110 and drawing current from the power supply in block 108 may continue as a procedure is performed with the tool assembly 20, including the tool tip 24, in block 112. Performing a procedure in block 112 and/or completing the procedure can include any selected procedure. For example, the tool tip 24 may exemplary be a burr hole drilling tool tip that is configured to form a burr hole in a skull 150 of a subject 152, as illustrated in FIG. 4. The creation of a burr hole 210 in the skull 150, however, is merely exemplary of appropriate or possible procedures. Other procedures may include placing a stent, placing a catheter, placing a deep brain stimulation probe, or the like within the subject. Further, the procedure need not be a skull procedure or neurological procedure and may include positioning a catheter within a vasculature of the subject, within the lungs of the subject, or other appropriate procedure. Nevertheless, during the performing of the procedure in block 112, communication with a navigation system of block 110 and a drawing of current from the power source in block 108 may occur. The current drawn in block 108 may allow the tracking device 30b to communicate information regarding location to the navigation system in block 112.

Once a procedure is completed, the tool assembly, including the tool tip 24, may enter a cleaning and charging sub-workflow 113. In the clean and charging 113 the tool assembly, including the tool tip 24 with the tracking device 30b, can be cleaned and sterilized in block 114. In various embodiments, cleaning and sterilizing may be performed with only or substantially only heat and/or steam according to generally known techniques. For example, heat and steam cleaning can be performed in an autoclave such as in an EZ9Plus™ fully automatic autoclave, Model 6690 Sterilizer, or other sterilizers such as those sold by Tuttnauer, having a place of business in Hauppauge, N.Y. Such sterilization systems generally generate heat and/or steam to clean and sterilize items placed therein. The cleaning and sterilization is a generally performed step in a medical setting to allow reuse of various tools and instruments. Other cleaning techniques may also heat the generator enough to cause the a current, but need not based solely on heat and steam. Various chemical cleaning techniques may also heat the generator 70 enough to cause a current to charge the battery 66. Thus, heat and steam cleaning is not required.

The heat and steam generated during the cleaning in step 114 can, then, activate the thermo-electric generator 70 to generate a current during the cleaning and sterilizing procedure in block 116. The generated current can be collected and stored in the power source 66 in block 118. In this way, the power source 66 can be recharged after one or more uses during a cleaning and sterilizing step in block 114. In other words, the power source 66 may be recharged without requiring a separate charging/recharging step. A cleaning and sterilization step may be used to charge and/or recharge the power source 66 that is usually performed on non-disposable instruments.

Therefore, the tracking device 30b can include a power supply that need not be replaced after one or more uses (e.g., a disposable battery) or recharged with a separate step and/or instrumentation. Due to the inclusion of the thermo-electric generator 70, in communication with the power source 66 of the tracking device 30, the power source 66 can be recharged during the cleaning procedure that generally includes heat and/or steam generation. Thus allowing an efficient recharging of the power supply for additional uses.

Following the cleaning and sterilization, the tool assembly 20 may be optionally stored in block 120. The work flow allows for continuous repetition and use of the tool assembly 20, as illustrated in the work flow 100 in FIG. 3. After the power is collected in the power supply in block 118, the work flow may immediately go to the decision block of whether the power supply is properly charged in block 102. Following the collection and storage of power in the power source 66 in block 118, generally the power supply is properly charged. If it is determined that the power supply is not properly charged, at the decision block 102, the NO path 126 may be followed to clean and sterilize, such as using heat and/or steam, in block 114. Therefore, cleaning the tool in a medical setting (e.g. in a hospital) may be followed to allow for regenerating and charging the power source 66, as illustrated in the work flow 100. It is understood, however, that a specific heat-generating system that may be provided to charge the power source 66 via the thermo-electric generator 70, but is not required.

The work flow 100 allows for the use, cleaning, and recharging of the power supply of the tracking device. The tracking device 30b can be used with a navigation system, such as a surgical navigation system 150 illustrated in FIG. 4. The navigation system 150 may be used similar to a navigation system generally known in the art, including the StealthStation® surgical navigation system sold by Medtronic, Inc. Nevertheless, the following discussion of the navigation system 150 is provided for illustration and completeness of the current discussion. Further, it is understood that the generator 70 and power source 66 may be provided in any appropriate device, such as the DRF tracking device 271.

With reference to FIG. 4, the instrument assembly, including the tool bit 24 may be positioned relative to, such as within, the subject 150 with a navigated instrument. The tool assembly 20, with the tracking device 30, may be a navigated instrument. As discussed above, the instrument assembly 20 is merely exemplary, and other navigated instruments may include catheters, leads, stimulators, etc. Also, the tracking device 30 may incorporated into a separate element, such as a removable stylet. The stylet may be placed within a lumen of a catheter.

The tracking device 30 may be interconnected with a navigation system 202, as illustrated in FIG. 4. The navigation system, as discussed further herein, may include a tracking system 204 that can track the tracking device 30 in three-dimensional space including a X, Y, Z location and various orientations to determine a position of the tracking device 30 in space. As illustrated above, the instrument 20 may include the tracking device 30 that allows for directly tracking the tool 20 during an implantation and positioning of tool 20. Appropriate tracking devices can include tracking devices as disclosed in U.S. Pat. No. 8,644,907, incorporated herein by reference. Additionally, the navigation system can include the navigation system disclosed in U.S. Patent Application Publication 2014/0323852, incorporated herein by reference.

With continuing reference to FIG. 4, the tool 20 may be used to form an opening or bore 210 in the skull 150 of the subject 152. The bore 210 may be a burr hole formed through the skull 150 as generally understood in the art. The tool 20 may be tracked either directly via the tracking device 30 or via the tracking device on a stylet or other portion associated with the tool 20. Further, as noted above, the tracking device may be associated directly with the tool tip 24 as the tracking device 30b or with another portion of the tool assembly 20. Thus, any one or more of these may be used to track the selected portion of the tool assembly 20.

The navigation of the tool assembly 20 relative to the subject 152 may proceed according to various navigation procedures and techniques, such as those generally known in the art and discussed below, to ensure or assist in positioning the catheter 10 in a selected, including a predetermined or preselected location, within the subject 152. Further, although the following description is related generally to positioning the tool assembly 20 relative to the skull 150 of the subject 152, other navigated procedures may be performed.

The navigation system 202, which may include an electromagnetic navigation system, is primarily described with respect to performing a procedure on a human patient, the navigation system 202 may be used to perform a procedure on other animate and/or inanimate subjects, including those navigation systems as disclosed in U.S. Pat. App. Pub. No. 2014/0323852, incorporated herein by reference. Also, procedures disclosed herein can be performed relative to a volume, a mechanical device, and/or an enclosed structure. The volume may be of an animate or inanimate object. The subject can be an object that includes an enclosed mechanical device.

The navigation system 202 assists in performing a navigated or guided procedure. The guided procedure can be, for example, a surgical procedure, a neural procedure, a spinal procedure, and an orthopedic procedure. The navigation system 202 allows a user, such as a surgeon 220, to view on a display 256 a position of the tool assembly 20 in a coordinate system. The coordinate system can be related to an image, such as in an image guided procedure, or can be related to an imageless procedure.

The navigation system 202 can operate as an image-based system or as an imageless system. While operating as an imageless system, the navigation system 202 can register a subject space (generally defined within and near the subject 152) to a graphical display representing an area of the subject 152, rather than to both the subject space and an image space. Image data of the subject 152 need not be acquired at any time, although image data can be acquired to confirm various locations of instruments or anatomical portions of the subject 152. Positions of the subject 152 can be tracked and positions of the tool assembly 20 relative to the subject 152 can be tracked.

While operating as an imageless system, a position of an anatomical structure can be determined relative to the instrument and the positions of the anatomical structure and the instrument can be tracked. For example, a plane of an acetabulum can be determined by touching several points with the tool assembly 20, or selected tracked tool with at least one of the tracking devices 30. As another example, a position of a femur can be determined in a similar manner. The position of the tool assembly 20 and the anatomical structure can be shown on a display with icons or graphics. The display, however, may not show actual image data captured of the subject 152. Other data can be provided, such as atlas data or morphed atlas data. The atlas data can be image data that is generated or generalized from the subject 152. For example, a brain atlas can be generated based on detail analysis of image data of a brain of a patient. Operation of the navigation system 202 as an image based system is further described below.

Although the navigation system 202 is described as acquiring image data using an imaging device 230, other data may be acquired and/or used, such as patient and non-patient specific data. The imaging device 230 acquires pre-, intra-, or post-operative image data and/or real-time image data of a subject 152. The imaging device 230 can be, for example, a fluoroscopic x-ray imaging device that may be configured as a C-arm having an x-ray source 232 and an x-ray receiving device 234. Other imaging devices may be included and mounted on the imaging device 230. Calibration and tracking targets and radiation sensors may be included.

The navigation system 202 may further include an imaging device controller 236. The imaging device controller 236 controls the imaging device 230 to (i) capture x-ray images received at the x-ray receiving section 234, and (ii) store the x-ray images. The imaging device controller 236 may be separate from the imaging device 230 and/or control the rotation of the imaging device 230. For example, the imaging device 28 can move in selected directions around the patient 152. Also, the imaging device may include an O-arm® imaging device as sold by Medtronic, Inc., having a place of business in Minnesota.

Further, an imager tracking device 240 may be included to track a position of selected portions of the imaging device 230 to identify the position of the imaging device 230 relative to the subject 152 while acquiring the image data to assist in registration. The image data can then be forwarded from the imaging device controller 236 to a processing module of a navigation computer 250 wirelessly or via a link 252. The navigation computer 250 can include a processing module that is configured to execute instructions to perform a procedure.

A work station 254 can include the navigation computer 250, a navigation display 256, a user interface 258, and an accessible memory system 260. The image data may be transmitted from the controller 236 to the work station 254 or to a tracking system 204. The workstation 254 may be a portable computer, such as a laptop computer or a tablet computer. The navigation computer 250 including the computer module may include a general purpose processor that executes instructions for navigating the tool assembly 20 and/or may include an application specific circuit. The tracking system 204, as discussed further herein, may include a coil array controller (CAC) 260 having a navigation device interface (NDI) 262.

While the imaging device 230 is shown in FIG. 4, any other alternative 2D, 3D or 3D imaging acquired over time to include four dimensions, imaging modality may also be used. For example, any imaging device, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative, computed tomography (CT), single photo emission computed tomography (SPECT), and/or planar gamma scintigraphy (PGS) imaging devices may be used. Any of these imaging devices may be used to acquire pre- or post-operative and/or real-time images or image data of the subject 152. The images may also be obtained and displayed, generally, in two or three dimensions. In more advanced forms, 3D surface rendering regions are achieved of the subject, which may be rendered or changed in time (fourth dimension). The 3D surface rendering regions may be achieved by incorporating subject data or other data from an atlas or anatomical model map or from pre-operative image data captured by MRI, CT, or echocardiography modalities. Image data sets from hybrid modalities, such as positron emission tomography (PET) combined with CT, or single photon emission computer tomography (SPECT) combined with CT, can also provide functional image data superimposed onto anatomical data to be used to reach target sites within the subject 152.

The navigation system 202 further includes the tracking system 204. The tracking system 204 includes a localizer 264, which may also be referred to as a transmit coil array (TCA), a tracking array, or a transmit coil assembly. The TCA 264 includes coil arrays 266 that can transmit or receive. The tracking system 204 includes the CAC 260. The localizer 264, the instrument tracking device 30 of the tool assembly 20. It is understood that the tracked portion may be generally referred to as an instrument and that the tracking device may be generally referred to as an instrument tracking device. The tracking system may also track a dynamic reference frame (DRF) 270. All tracked portions are connected to the CAC 260 via the NDI 262. The CAC 260 and the NDI 262 can be provided in a CAC/NDI container 272. The NDI 262 may have communication ports that communicate with the localizer 264, the instrument tracking device 30 and/or the DRF 270 wirelessly or via wires.

The coil arrays localizer 270 can transmit signals that are received by the DRF 270 and at least one tracking device (e.g., the instrument tracking device 30). The tracking device 30 can be associated with the tool assembly 20 at a location that is generally positioned within the subject 152 during a procedure. The DRF 270 can then transmit and/or provide signals, from a DRF tracking device 271, based upon the received/sensed signals of the generated fields from the localizer 270 and/or other localizers. It is understood that the tracking system may also be operated in reverse, where the tracking devices 30, 270 transmit a field that is sensed by the TCA 270.

The DRF 270 can be connected to the NDI 262 to forward the information to the CAC 260 and/or the navigation computer 250. The DRF 270 may be fixed to the subject 152 and adjacent to the region where navigation is occurring such that any movement of the subject 152 is detected as relative motion between the localizer 264 and the DRF 270. The DRF 270 can be interconnected with the subject 152. Any relative motion is indicated to the CAC 260, which updates registration correlation and maintains accurate navigation.

In operation, the navigation system 202 creates a map between points in image data or an image space, such as one defined by an image 280 shown on the display 256, and corresponding points in a subject space (e.g., points in an anatomy of a patient or in a patient space). After the map is created, the image space and subject space are registered to each other. This includes correlating position (location and orientations) in an image space with corresponding positions in a subject space (or real space). Based on the registration, the navigation system 202 may illustrate an icon 282 (which may include a three-dimensional rendering of the instrument, including the tool assembly 20) at a navigated position of the tool assembly 20 relative to an image of the subject 152 in a super-imposed image. For example, the icon 282 can be illustrated relative to a proposed trajectory and/or a determined anatomical target. The work station 254 alone and/or in combination with the CAC 260 and/or the C-arm controller (or control module) 236 can identify the corresponding point on the pre-acquired image or atlas model relative to the tracked tool assembly 20; and display the position on display 256 and relative to the image 280. This identification is known as navigation or localization. The work station 254, the CAC 260, and the C-arm controller 236 and/or selected portions thereof can be incorporated into a single system or implemented as a single processor or control module.

To register the subject 152 to the image 280, the user 220 may use point registration by selecting and storing particular points from the pre-acquired images and then touching the corresponding points on the subject 152 with a pointer probe or any appropriate tracked device. The navigation system 202 analyzes the relationship between the two sets of points that are selected and computes a match, which allows for a correlation of every point in the image data or image space with its corresponding point on the subject 152 or the subject space.

The points that are selected to perform registration or form a map are the fiducial markers, such as anatomical or artificial landmarks. Again, the fiducial markers are identifiable on the images and identifiable and accessible on the subject 152. The fiducial markers can be artificial landmarks that are positioned on the subject 152 or anatomical landmarks that can be easily identified in the image data.

The navigation system 202 may also perform registration using anatomic surface information or path information (referred to as auto-registration). The navigation system 202 may also perform 2D to 3D registration by utilizing the acquired 2D images to register 3D volume images by use of contour algorithms, point algorithms or density comparison algorithms.

In order to maintain registration accuracy, the navigation system 202 tracks the position of the subject 152 during registration and navigation with the DRF 270. This is because the subject 152, DRF 270, and localizer 264 may all move during the procedure. Alternatively the subject 152 may be held immobile once the registration has occurred, such as with a head holder. Therefore, if the navigation system 202 does not track the position of the subject 152 or an area of an anatomy of the subject 152, any subject movement after registration would result in inaccurate navigation within the corresponding image. The DRF 270 allows the tracking system 204 to track the anatomy and can be used during registration. Because the DRF 270 is rigidly fixed to the subject 152, any movement of the anatomy or the localizer 264 is detected as the relative motion between the localizer 264 and the DRF 270. This relative motion is communicated to the CAC 260 and/or the processor 250, via the NDI 262, which updates the registration correlation to thereby maintain accurate navigation.

The tracking system 204 can position the localizer 270 adjacent to the patient space to generate an EM field (referred to as a navigation field). Because points in the navigation field or patient space is associated with a unique field strength and direction, the tracking system 204 can determine the position (which can include location and orientation) of the tool assembly 20 by measuring the field strength and direction or components of the EM field at the tracking device 30. The DRF 270 is fixed to the subject 152 to identify the location of the subject 152 in the navigation field. The tracking system 204 continuously determines the relative position of the DRF 270 and the tool assembly 20 during localization and relates this spatial information to subject registration data. This enables image guidance of the tool assembly 20 within and/or relative to the subject 152.

To obtain a maximum accuracy it can be selected to fix the DRF 270 in each of at least six degrees of freedom. Thus, the DRF 270 or any tracking device, such as the tracking device 30, can be fixed relative to axial motion X, translational motion Y, rotational motion Z, yaw, pitch, and roll relative to a portion of the subject 152 to which the DRF 270 is attached. Any appropriate coordinate system can be used to describe the various degrees of freedom. Fixing the DRF 270 relative to the subject 152 in this manner can assist in maintaining maximum accuracy of the navigation system 202.

The tool assembly 20 can include the stylet, drill, etc., as discussed above. Thus, reference to the tool assembly 20 is not intended to limit the instrument that may be tracked and navigated. With reference to any appropriate navigated instrument, it may include the tracking device 30 that may include the power source 66 and generator 70. The power supply may be charged, as discussed above, and the tool may be tracked with the navigation system as discussed above.

Further, it is understood that the power source 66 and the generator 70 may be provided with any appropriate powered device. An implantable medical device may include the thermo-electric generator 70 connected to the power source 66. For example, an IMD may include a cardiac stimulator or neural stimulator that includes a power source to provide stimulation and rhythm regulation. The power source may be drained over time when providing the selected stimulation and rhythm regulation. Temperature differentials within a selected subject may be used to generate a current with the thermo-electric generator 70 therein.

The wireless communications described in the present disclosure can be conducted in full or partial compliance with IEEE standard 802.11-2012, IEEE standard 802.16-

2009, IEEE standard 802.20-2008, and/or Bluetooth Core Specification v4.0. In various implementations, Bluetooth Core Specification v4.0 may be modified by one or more of Bluetooth Core Specification Addendums 2, 3, or 4. In various implementations, IEEE 802.11-2012 may be supplemented by draft IEEE standard 802.11ac, draft IEEE standard 802.11ad, and/or draft IEEE standard 802.11ah.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of powering an instrument, comprising:
operating an instrument to draw power from a power source;
cleaning the instrument with heat to at least charge the power source with a provided thermo-electric generator when exposed to a selected temperature differential between a first contact and a second contact of the thermo-electric generator; and
providing the instrument to include at least a tracking sensor operably connected to the thermo-electric generator;
wherein the power source powers the tracking sensor.

2. The method of claim 1, wherein heat cleaning the instrument includes simultaneously sterilizing the instrument and charging the power source.

3. The method of claim 1, further comprising:
preparing the instrument for a procedure including determining whether the power source has a predetermined charge.

4. The method of claim 1, further comprising:
drawing a current from the power source to operate the tracking sensor for tracking the instrument.

5. The method of claim 2, wherein heat cleaning includes autoclaving the instrument.

6. The method of claim 4, wherein drawing current from the power source to operate the tracking sensor for tracking the instrument includes drawing a current from the power source to sense a navigation field or transmit sensed field information to a navigation system.

7. A method of powering an instrument, comprising:
operating an instrument to draw power from a power source;
cleaning the instrument with heat to at least charge the power source with a provided thermo-electric generator when exposed to a selected temperature differential between a first contact and a second contact of the thermo-electric generator; and
operating a localizer to emit an electromagnetic field to be sensed by a tracking device powered by the power source.

8. The method of claim 7, further comprising:
providing the tracking device to include at least a coil of conducting material to sense the emitted electromagnetic field.

9. The method of claim 7, wherein operating a localizer to emit an electromagnetic field includes operating an electromagnetic navigation system having the localizer.

10. The method of claim 7, further comprising:
providing the thermo-electric generator in the instrument.

11. The method of claim 7, further comprising:
providing the tracking device at a tip of the instrument.

12. The method of claim 7, further comprising:
providing a subject tracking device configured to be fixed to a subject;
wherein the subject tracking device includes a second thermo-electric generator to charge a second power source included with the subject tracking device.

* * * * *

UNITED STATES PATENT AND TRADEMARK OFFICE
CERTIFICATE OF CORRECTION

PATENT NO. : 11,684,451 B2
APPLICATION NO. : 16/936644
DATED : June 27, 2023
INVENTOR(S) : Andrew Bzostek et al.

It is certified that error appears in the above-identified patent and that said Letters Patent is hereby corrected as shown below:

On the Title Page

Page 2, Column 2, Other Publications, Line 8, Delete "16/674,630" and insert --14/674,630-- therefor In the Specification Column 3, Detailed Description, Line 28, Delete "20" and insert --24-- therefor Column 7, Detailed Description, Line 65, Delete "150" and insert --202-- therefor Column 7, Detailed Description, Line 66, Delete "150" and insert --202-- therefor Column 8, Detailed Description, Line 3, Delete "150" and insert --202-- therefor Column 8, Detailed Description, Line 10, Delete "150" and insert --152-- therefor Column 9, Detailed Description, Line 57, Delete "28" and insert --230-- therefor Column 10, Detailed Description, Line 63, Delete "270" and insert --264-- therefor Column 11, Detailed Description, Line 4, Delete "270" and insert --264-- therefor Column 12, Detailed Description, Line 20, Delete "270" and insert --264-- therefor Signed and Sealed this
Seventeenth Day of October, 2023

*Katherine Kelly Vidal*

Katherine Kelly Vidal
*Director of the United States Patent and Trademark Office*